(12) United States Patent
Clancy et al.

(10) Patent No.: US 10,874,379 B2
(45) Date of Patent: Dec. 29, 2020

(54) SAMPLE RETRIEVAL DEVICE AND METHOD OF USE THEREOF

(71) Applicant: COOK MEDICAL TECHNOLOGIES LLC, Bloomington, IN (US)

(72) Inventors: Michael S. Clancy, Monaleen (IE); Patrick Dennis, Clontarf (IE); Fionan Keady, County Galway (IE)

(73) Assignee: Cook Medical Technologies LLC, Bloomington, IN (US)

( * ) Notice: Subject to any disclaimer, the term of this patent is extended or adjusted under 35 U.S.C. 154(b) by 531 days.

(21) Appl. No.: 15/715,419

(22) Filed: Sep. 26, 2017

(65) Prior Publication Data

US 2018/0085099 A1    Mar. 29, 2018

Related U.S. Application Data

(60) Provisional application No. 62/400,188, filed on Sep. 27, 2016, provisional application No. 62/522,909, filed on Jun. 21, 2017.

(51) Int. Cl.
*A61B 10/00* (2006.01)
*A61B 10/02* (2006.01)
*A61B 10/04* (2006.01)

(52) U.S. Cl.
CPC .......... *A61B 10/0233* (2013.01); *A61B 10/04* (2013.01); *A61B 2010/045* (2013.01)

(58) Field of Classification Search
CPC ................ A61B 10/0233; A61B 10/04; A61B 2010/045; A61B 2090/3908
See application file for complete search history.

(56) References Cited

U.S. PATENT DOCUMENTS

| | | | |
|---|---|---|---|
| 3,859,998 A | 1/1975 | Thomas et al. | |
| 4,693,257 A | 9/1987 | Markham | |
| 5,494,044 A * | 2/1996 | Sundberg | A61B 10/0048 600/562 |
| 5,928,199 A | 7/1999 | Nakagami | |
| 6,520,954 B2 | 2/2003 | Ouchi | |
| 7,233,820 B2 | 6/2007 | Gilboa | |
| 7,544,184 B2 | 6/2009 | Cope et al. | |
| 2002/0095069 A1 | 7/2002 | Dhindsa | |
| 2004/0260199 A1 | 12/2004 | Hardia, Jr. et al. | |
| 2004/0260274 A1 * | 12/2004 | Hardin | A61B 10/04 606/1 |
| 2006/0149222 A1 | 7/2006 | Okada | |

(Continued)

OTHER PUBLICATIONS

Invitation to Pay Additional Fees in corresponding International Application No. PCT/US2017/052145, dated Dec. 20, 2017, 11 pages.

(Continued)

*Primary Examiner* — Christian Jang
(74) *Attorney, Agent, or Firm* — Brinks, Gilson & Lione

(57) ABSTRACT

One aspect of the present invention generally relates to a sample retrieval device and to system including such a device in combination with biopsy needle. Another aspect of the invention provides a method of using the sample retrieval device in combination with the biopsy needle to retrieve a biopsy sample from a patient and to prepare the sample for examination.

4 Claims, 25 Drawing Sheets

(56) References Cited

U.S. PATENT DOCUMENTS

| | | | |
|---|---|---|---|
| 2014/0005478 A1* | 1/2014 | Kennedy, II | A61B 1/012 600/114 |
| 2014/0180164 A1 | 6/2014 | McGhie | |
| 2014/0257136 A1 | 9/2014 | Leahy et al. | |
| 2015/0087994 A1 | 3/2015 | Matsuno et al. | |

OTHER PUBLICATIONS

International Search Report and Written Opinion in corresponding International Application No. PCT/US2017/052145, dated Mar. 7, 2018, 19 pages.

* cited by examiner

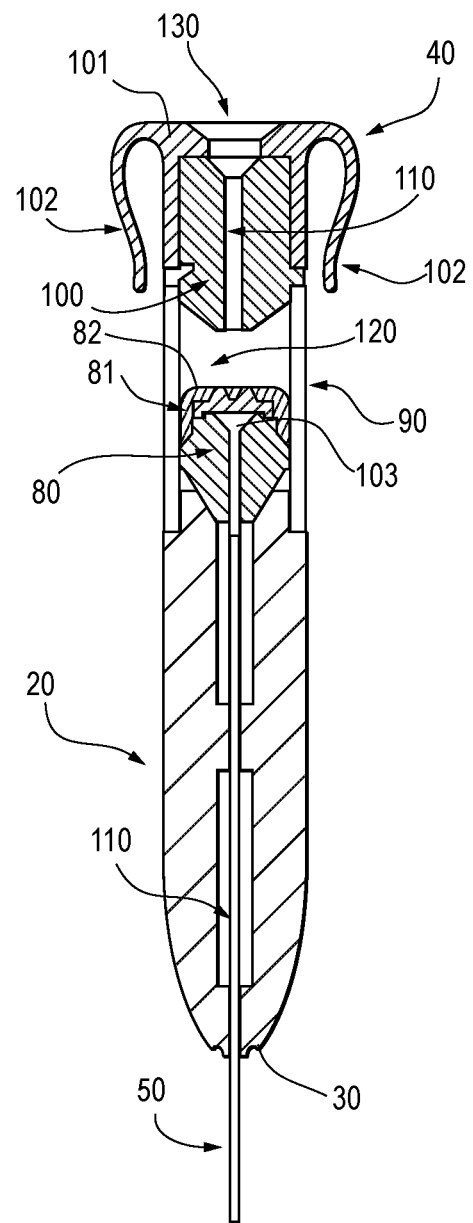

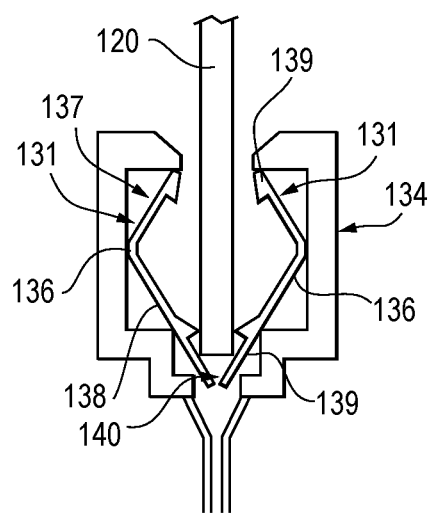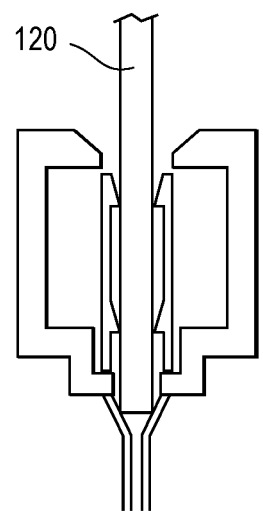
Fig. 14A
Fig. 14B

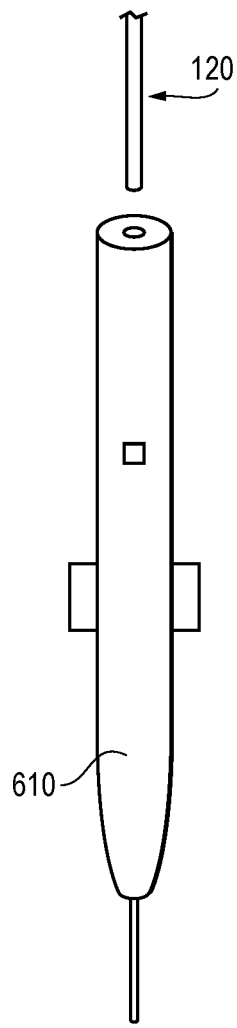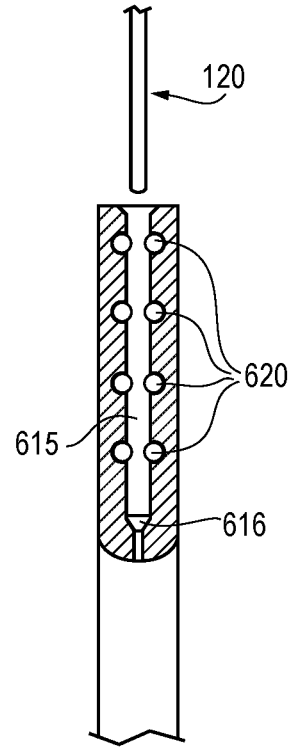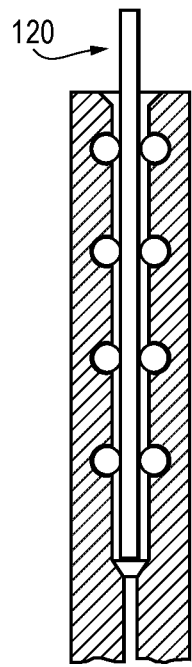

SAMPLE RETRIEVAL DEVICE AND METHOD OF USE THEREOF

RELATED APPLICATIONS

The present patent application claims the benefit of the filing date under 35 U.S.C. § 119(e) of U.S. Provisional Patent Application Nos. 62/400,188, filed Sep. 27, 2016, and 62/522,909, filed Jun. 21, 2017, the contents of which applications is hereby incorporated by reference.

TECHNICAL FIELD

One aspect of the present disclosure relates generally to a sample retrieval device and to system including such a device in combination with biopsy needle. Another aspect of the disclosure provides a method of using the sample retrieval device in combination with the biopsy needle during the retrieval of a biopsy sample from a patient and in the preparation of the sample for examination.

BACKGROUND

Current methods of Endoscopic Ultrasound ("EUS") sample retrieval are undefined. Doctors and nurses must employ many different techniques in order to retrieve a sample from an EUS needle. This is also the case in rapid on-site evaluation ("ROSE"). These factors put the users at great risk of needle-stick injury and also present a high risk for sample contamination. There is the need for a device that protects users from needle stick injury during EUS sample retrieval. Likewise, there is the need for a device that gives the user control over the needle during EUS procedures, helping to greatly reduce the risk of contamination.

ROSE is a method used by pathologists and cytotechnologists to quickly evaluate samples taken in Endoscopic Ultrasound Fine Needle Aspiration ("EUS/FNA") procedures. The process involves expelling the sample from the needle onto a glass cytology slide. This is achieved by attaching a syringe primed with air to the proximal end of the needle and flushing the contents of the needle to produce a sample. A smear is then created and the pathologist/cytotechnologist can then begin preparing the sample for evaluation.

The current method by which a sample is expelled from the EUS needle can involve up to 3 members of the clinical staff. Typically, the doctor will remove the needle from the endoscope and bring it to the area where the slides are being made. Prior to the sample being collected, cytology slides will have been placed on a suitable working surface by a member of the clinical staff ready to receive a sample. The doctor will then extend the needle tip by several centimeters and lock the device before passing the handle of the needle to another member of the clinical staff who removes a vacuum source utilized in obtaining the sample from a patient and attaches a syringe which has been primed with air or saline.

At this stage the doctor will hold the tip of the needle over a cytology slide and will ask for the needle to be flushed with fluid, thus producing a sample. The needle may be flushed several times with both air and saline to ensure that no biopsy material remains in the needle cannula. A stylet is then re-inserted into the needle by the doctor or another member of the clinical staff. Re-insertion of the stylet is difficult and can involve more than one person.

Finally the needle is withdrawn into its sheath and is locked in place. At this point the slide onto which the sample was produced is smeared and prepared for evaluation by the pathologist/cytotechnologist. If the sample is not expelled from the needle in time it can coagulate and clog the needle rendering it unusable. Additionally the amount of time that the sample is exposed to air can alter its properties and have a negative effect on evaluation.

The process of producing a sample onto a slide is both time-consuming and potentially dangerous. EUS/FNA needles are extremely sharp and very difficult to handle due to their length and flexibility. The unmanageable nature of the needle becomes dangerous once the needle is exposed and the risk of needle-stick injury and thus transmission of blood-borne viruses increases.

Although EUS needles generally have a built-in safety lock which, once engaged, makes the needle perfectly safe to handle, when the needle is intentionally exposed for sample retrieval or if the user fails to engage the safety lock the device becomes unsafe. The EUS needle can be extended up to 8.5 cm and if mishandled is susceptible to bending or kinking. If a needle kinks it can no longer be used and must be disposed in an appropriate waste receptacle.

SUMMARY

In one aspect, the present invention provides a sample retrieval device including an elongated body having a longitudinal axis extending from the first end to the second end. In some embodiments, the second end may be tapered. In one embodiment a cannula is positioned within to and extends from the second end in a direction of the longitudinal axis. A lumen extends from the first end to the second end and through the cannula. An attachment member attaches to the elongated body. The attachment member may be a C-clamp and, in some embodiments, the attachment member is orientated to facilitate attachment of the device substantially perpendicular to the longitudinal axis of an elongated device, for example, a biopsy needle handle, positioned in the C-clamp.

The device may also include a non-return valve positioned within the elongated body and in-line with the lumen. In some embodiments, a portion of the lumen between the first end and the non-return valve is expanded to form a cavity within the elongated body of the device. The wall of the elongated body may include a transparent portion allowing a user to view the interior of the cavity.

The elongated body may be at least partly formed from a polymer. In some embodiments, the cannula extending from the elongated body is formed from a transparent or translucent material, allowing the user to observe objects contained within that portion of the cannula. In some embodiments, the first end of the elongated body includes a recessed portion around the entrance to the lumen.

Another aspect of the invention provides a system including a biopsy needle and a sample retrieval device as disclosed herein. In one embodiment, the biopsy needle includes a handle having a proximal handle segment and a distal handle segment, and a sheath attaching to and extending distally from the distal handle segment. A lumen extends through the handle and sheath from the proximal end of the proximal handle segment to a distal end of the sheath. A biopsy needle cannula is positioned within the lumen and includes open proximal and distal ends and a cannula lumen extending therebetween. The biopsy needle cannula is slidably movable through a portion of the lumen between a first position where the distal end of the biopsy needle cannula is contained within the lumen of the sheath and a second position where the distal end of the biopsy needle cannula extends distally from the sheath.

The portion of the retrieval device lumen at the first end is sized to accept the sheath and to hold the distal end of the sheath and a portion of the retrieval device lumen at the second end and through the retrieval cannula is sized to accept the biopsy needle cannula. The attachment member is sized to attach to and hold the handle of the biopsy needle. In some embodiments, the attachment member is sized to attach to and hold the handle at a substantially perpendicular orientation to the longitudinal axis of the sample retrieval device.

In one embodiment, the proximal handle segment slidably engages the distal handle segment. In this embodiment, the proximal end of the biopsy needle cannula attaches to the proximal handle segment and the retrieval cannula is of a length sufficient to enclose the distal end of the biopsy needle cannula when the proximal handle segment slidably engages the distal handle segment at a fully distal position and when the distal end of the sheath is positioned at the non-return valve.

In one embodiment, the biopsy needle also includes a stylet sized to be slidably movable within the biopsy needle cannula lumen.

Another aspect of the invention provides a method of retrieving a sample contained within a biopsy needle. In one embodiment, the method includes attaching a sample retrieval device as disclosed herein to a handle of the biopsy needle as disclosed herein. In one embodiment, the sample retrieval device is attached to the handle by an attachment member as described herein.

The distal end of the sheath of the biopsy needle is inserted into the lumen at the first end of the elongated body of the sample retrieval device. The biopsy needle cannula is then advanced distally through the retrieval device cannula to position the distal end of the biopsy needle cannula within that region of the retrieval device cannula that extends from the body of the sample retrieval device. A fluid at pressure is introduced through the proximal end to the biopsy needle cannula in an amount and at a pressure sufficient to expel the sample from the biopsy needle.

Yet another aspect of the invention provides a system including a biopsy needle having a handle and a sheath extending distally from the distal end of the handle. The sheath includes a stop positioned near its distal end. The system also includes a sample retrieval device including a body having a lumen extending from its proximal end to its distal end. The sheath extends through the lumen and the sample retrieval device is free to slide over the sheath. The stop is of a dimension sufficient to prevent distal movement of the proximal end of the retrieval device beyond the stop.

BRIEF DESCRIPTION OF THE DRAWINGS

FIG. 3(A) is a cross section view of a sample retrieval device according to one embodiment of the present invention.

FIG. 11(A-C) are illustrations showing a one embodiment of a sample retrieval device including a splash guard.

FIG. 14(A-B) are illustrations showing yet another embodiment of a mechanism for holding a sheath within the lumen of the sample retrieval device.

FIG. 16(A-C) are illustrations showing yet another embodiment of a mechanism for holding a sheath within the lumen of the sample retrieval device. FIG. 16(B) is a partial cross section of FIG. 16A. FIG. 16(C) is an enlargement of a portion of FIG. 16(B).

FIG. 19(A-B) are illustrations of the sample retrieval device of FIG. 18 in combination with a biopsy needle.

DETAILED DESCRIPTION OF THE PREFERRED EMBODIMENTS

Definitions

Figure 1:
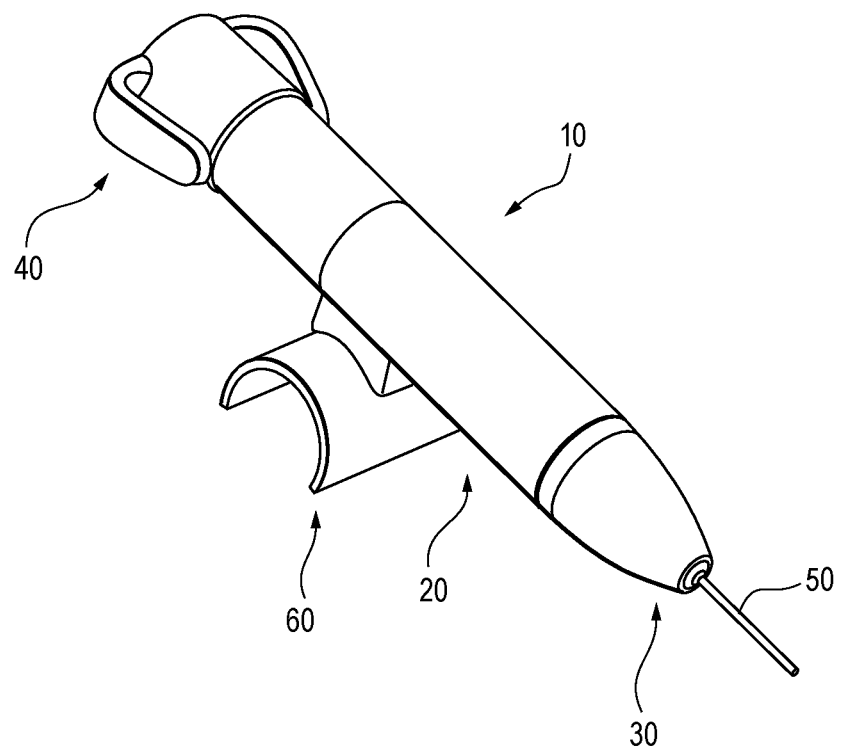
FIG. 1 is an illustration of a sample retrieval device according to one embodiment of the present invention.

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the device, as well as the axial ends of various component features. The term "proximal" is used in its conventional sense to refer to the end of the device (or component) that is closest to the medical professional during use of the assembly. The term "distal" is used in its conventional sense to refer to the end of the device (or component) that is initially inserted into the patient, or that is closest to the patient during use. The term "longitudinal" will be used to refer to an axis that aligns with the proximal-distal axis of the device (or component). The term "lateral" will be used to refer to an axis or plane that is perpendicular to the proximal-distal axis of the device (or component).

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

Biopsy Sample Retrieval Device

One aspect of the invention relates generally to endoscopic surgical devices. More particularly, this aspect of the invention pertains to a sample retrieval device for use with a biopsy needle during minimally-invasive procedures, such as endoscopic procedures.

One embodiment of a sample retrieval device will now be described with reference to FIGS. 1, 2 and 3. Turning first to FIG. 1, this figure shows a view of sample retrieval device 10. Sample retrieval device 10 includes elongated body 20 having a longitudinal axis extending from a first end 40 to a second end 30. Retrieval cannula 50 extends from second end 30. In a preferred embodiment, retrieval cannula 50 extends in the direction of the longitudinal axis. However, the present embodiments include those in which the retrieval cannula extends distally from second end 30 at an acute angle to the longitudinal axis. Preferably, retrieval cannula 50 is straight as is illustrated in FIG. 1. However, in other embodiments, retrieval cannula 50 may be curved.

In another embodiment, retrieval cannula 50 is rigid so as to provide protection against kinking of a biopsy needle cannula contained in the lumen of the cannula. The elongated body may have a "pen-like" shape including a rounded lateral cross-section and a tapered second end as illustrated in FIG. 1.

A retrieval device lumen (illustrated in FIG. 3) extends from first end 40, through elongated body 20 to second end 30 and through retrieval cannula 50. In some embodiments, retrieval cannula 50 extends into the retrieval device lumen. As will be explained in detail herein, a portion of the retrieval device lumen at first end 40 is sized to accept the sheath of a biopsy needle and to hold the distal end of the sheath. In one embodiment, the distal end of the sheath is held in place by a non-return valve positioned in-line with the retrieval device lumen. In this embodiment, the presence of the non-return valve acts to ensure that blood or tissue cannot pass back through the device when the sample is expelled from the needle cannula. As will be explained in more detail below, other mechanisms may be utilized to position and hold the distal region of the sheath at a fixed known position (engaged position) within the lumen.

In one embodiment, first end 40 includes a recessed portion surrounding the entry to the retrieval device lumen. This portion may act as a guide and provide for easier insertion of the sheath into the retrieval device lumen. In another embodiment, the portion of the sample retrieval device between first end 40 and the non-return valve is of a sufficient length to provide for straightening of the sheath and by doing so ensure that the needle cannula within the sheath exits in a straight line, so as to prevent kinking of the needle cannula. In various embodiments, the distance between the first end 40 and the non-return valve is greater than 0.5, 1.0, 1.5, 2.0, 2.5 or 3.0 inches. In another embodiment, a portion of the retrieval device lumen at second end 30 and through retrieval cannula 50 is sized to accept a cannula contained within the sheath, but not the sheath itself.

Figure 10A:
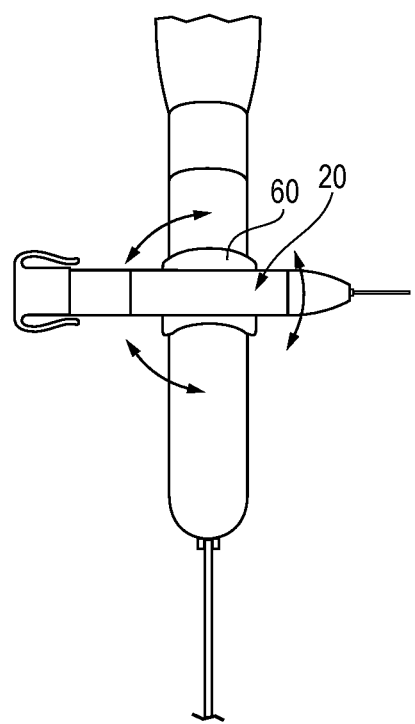
FIG. 10(A) is an illustration showing an attachment member allowing for rotation of the sample retrieval device with respect to the biopsy needle.

In yet another embodiment, attachment member 60 attaches to elongated body 20. Attachment member 60 may be sized and shaped to attach to and hold the handle of a biopsy needle at a substantially perpendicular orientation to the longitudinal axis of sample retrieval device 10. In some embodiments, the attachment member is a C-clamp. In other embodiments, the attachment member may be, for example, a strap or a magnetic attachment. The attachment member may provide for attachment of the device to a biopsy needle at a fixed orientation, for example, perpendicular to the longitudinal axis of the needle or at a non-perpendicular angle to the longitudinal axis. However in some embodiments, the biopsy needle and sample retrieval may be attached so that they may be rotated with respect to each other. For example, a rotatable C-clamp or strap may be attached to the sample retrieval device. FIG. 10(A) illustrates attachment member 60 attaching to elongated body 20 in a manner that allows rotation of the sample retrieval device with respect to the biopsy needle. In some embodiments, the sample retrieval device may be locked at fixed angular positions with respect to the longitudinal axis of the biopsy needle.

Figure 10B:
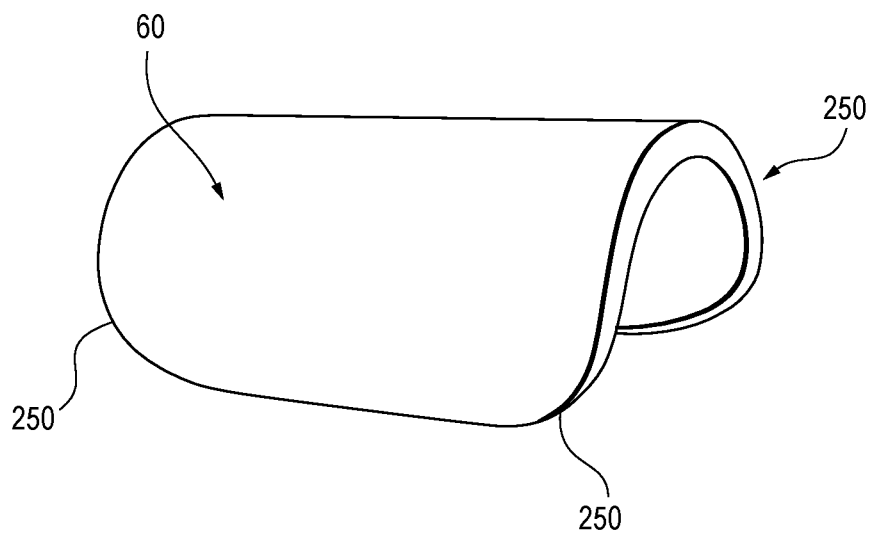
FIG. 10(B) is an illustration showing a C-clamp having fillets at the corners of the clamp.

FIG. 10(B) illustrates another embodiment of C-clamp 60. Here, the clamp includes fillets 250 at the corners of the clamp. Fillets 250 provide for easier attachment and detachment from the biopsy needle, adding to the ease of use of the sample retrieval device.

Figure 2A:
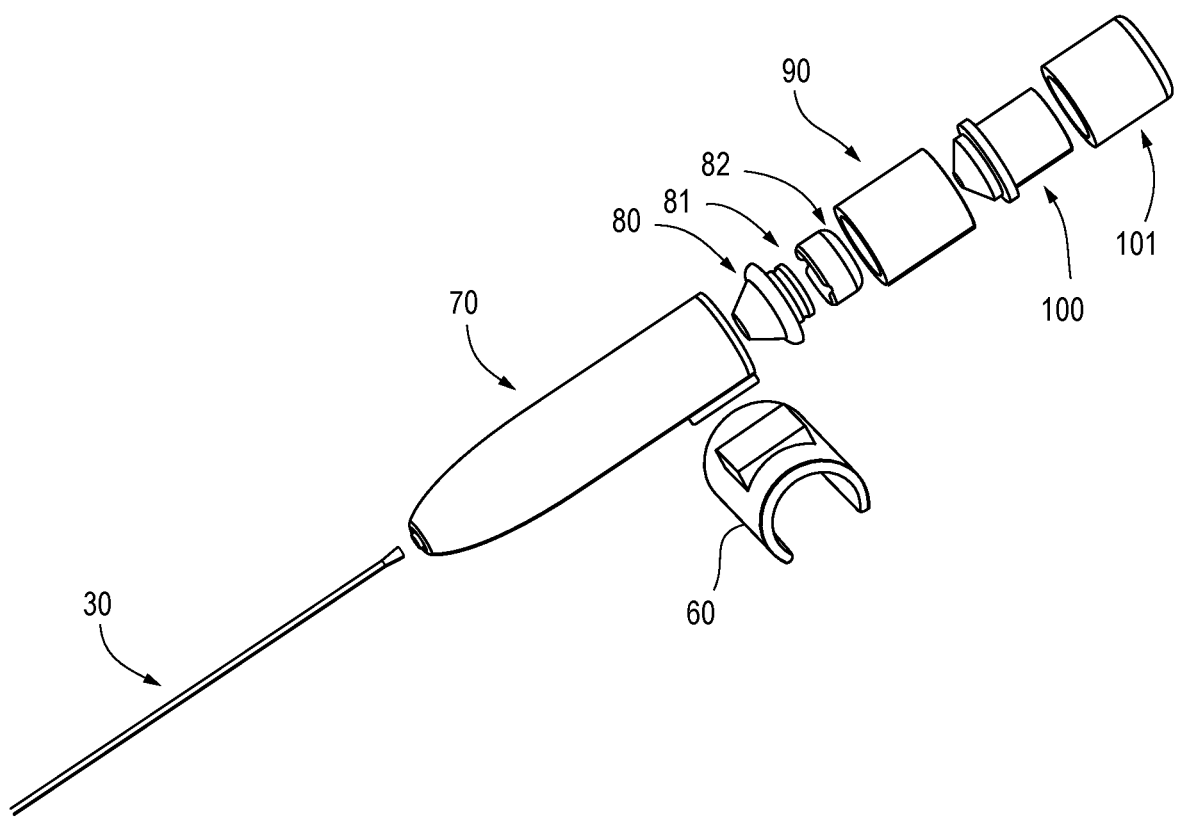
FIG. 2(A) is an illustration of an exploded view of the sample retrieval device of FIG. 1.

Turning now to FIG. 2(A), there is shown an exploded view of sample retrieval device 10. Here, attachment member 60 attaches to portion 70 of elongated body 20. Non-return valve components 80 to 82 are illustrated positioned between portions 70 and 100 of elongated body 20. In one embodiment, the non-return valve includes components 80 to 82. Here, component 82 is an outer cap, which may be formed for a plastic material. Component 81 forms the inner diaphragm of the valve, which may be formed from a rubber or rubber like material. Components 81 and 82 are clipped to component 80, which holds the valve in position within the device. In one embodiment, the distal end of the sheath of a biopsy needle is advanced to the non-return valve and passed through component 80. Component 80 holds the exterior or the sheath and ensures that no material is allowed to pass back through the lumen to the top of the device when the sample is expelled.

In the embodiment illustrated in FIGS. 1 and 2(A), member 90 joins bottom portion 70 to top portions 100 and 101. In some embodiments member 90 is translucent or transparent and provides the operator with a view of the non-return valve. When the distal tip of the sheath of a biopsy needle is inserted into the retrieval device lumen, the tip of the sheath will be visible through member 90, allowing for easier placement of the tip into the non-return valve and to ensure that the sheath is positioned at the proper engagement position. In some embodiments, the distal portion of the sheath may include a depth marker to visually indicate to the user when the sheath is inserted sufficiently into the device.

Figure 2B:
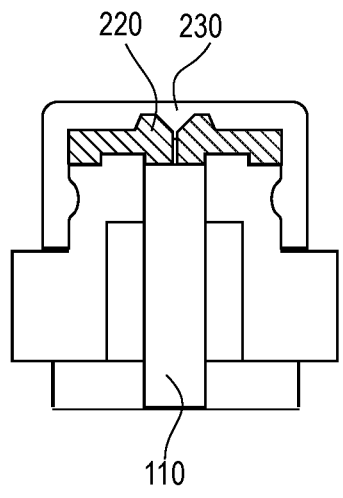
FIGS. 2(B-C) are enlarged views showing two embodiments of the non-return valve.
Figure 2C:
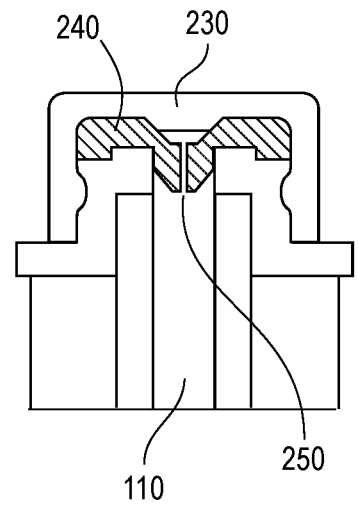

FIGS. 2(B) and 2(C) show cross section views of the non-return valve portion of the retrieval device. Turning first to FIG. 2(B). Here, non-return valve diaphragm 220 extends across retrieval device lumen 110. Valve orifice is sized to all passage of the sheath of the biopsy needle and to seal when the sheath is in position so as to prevent any return of fluid around the exterior of the sheath. The diaphragm across the lumen but does not extend downwards into the lumen.

FIG. 2(C) shows an alternative embodiment of the non-return valve. Here, lower portion 250 of valve diaphragm 240 is convex such that it extends downwards into the lumen. When the sheath of the biopsy needle passes through the valve orifice, the lower portion of the valve is pushed downward into the lumen eventually wedging the sheath. Such a design provides to the correct positioning of the sheath within the lumen of the device.

FIG. 3(A) shows a cross-sectional view of a sample retrieval device, illustrating the internal structure of one embodiment of the device. Here, retrieval device lumen 110 is shown as extending from first end 40 to second end 30 of the device. An entry to retrieval device lumen 110 is positioned at first end 40 and may include expanded entry port 130, which can act as a guide in positioning the sheath of the biopsy needle in retrieval device lumen 110.

Members 100 and 101 include a first (top) portion of retrieval device lumen 110. Members 100 and 101 may be separate components, as is illustrated in FIG. 2(A), or alternatively may be a single component forming the top portion of elongated body 20. In some embodiments, a portion of sample device lumen 110 below members 100 and 101 is expanded to form a cavity 120 within elongated body 20, as is illustrated in FIG. 3(A). Here, member 90 connects the top and bottom portions of the device and defines the lateral limits of cavity 120. If transparent or translucent, member 90 allows the operator to view the interior of cavity 120. The present embodiments include those in which only a portion of member 90 is transparent or translucent or in which this element is opaque.

In another embodiment, the proximal end of the device includes a Tuohy-Borst valve, through which the user will insert the sheath. This valve acts as both a control for slowing down the insertion speed (to reduce potential of kinking) and as a locking device for the sheath. By locking the sheath in position the possibility of the sheath slipping out of the device are reduced. Hence, the user can be sure that the sheath is posited at the engaged position such that the needle cannula, when fully extended, will not extend beyond the distal tip of retrieval cannula 50.

Figure 21:
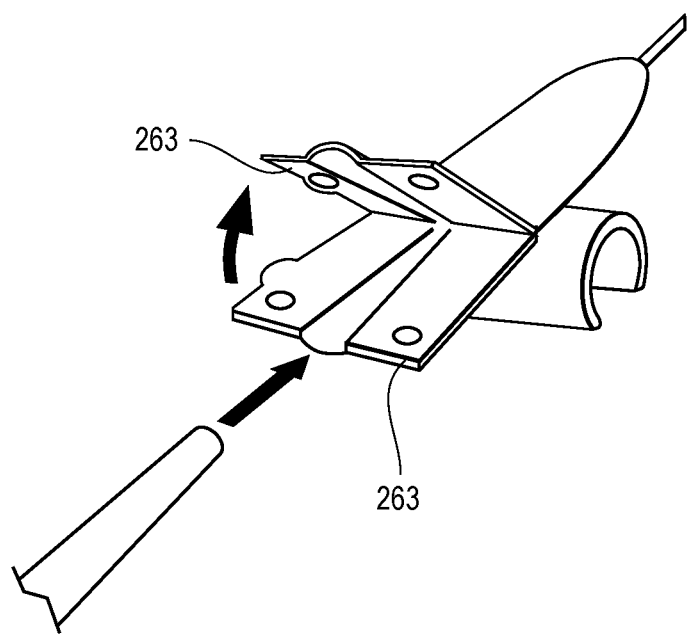
FIG. 21 is another embodiment of sample retrieval device of the present invention.

In yet another embodiment, the proximal portion of the device includes a clamp and an associated hinge. Such an embodiment is shown in FIG. 21. The user may open the clamp portions 263 and insert the sheath into the device. The clamp is then closed. By allowing the user to load the sheath into the device from the side, as opposed to from the proximal end, the user has a high degree of confidence that the sheath is positioned correctly.

In other embodiments, the sample retrieval device includes a view port which extends along a portion of the longitudinally axis of the device. Such a view port provides the operator with a view of the position of the sheath when it is positioned within the device. If the retrieval cannula is formed from a transparent material, the view port, if of sufficient length, also provides a view of the needle cannula when extended from the sheath. In such embodiments, an extended view port also increases the amount of light entering the device and improves visibility of the needle cannula within the retrieval cannula.

In FIG. 3(A), non-return valve components 80-82 are positioned below cavity 120. In one embodiment, the non-return valve is sized to accept and hold the distal end of the sheath at the engaged position and to prevent the distal end of the sheath from extending further into retrieval device lumen 110. For example, the lumen of component 80 may include a step down in diameter 103 to limit the travel of the sheath. In this embodiment, that portion of retrieval device lumen 110 between the non-return valve and retrieval cannula 50 is sized to accept a cannula contained within the lumen of the sheath, but not the sheath itself. Retrieval cannula 50 is contained within retrieval device lumen 110 and also extends from second end 30 of the device. In some embodiments, retrieval cannula 50 extends through retrieval device lumen 110 as far as the non-return valve. The lumen of retrieval cannula 50 also accepts a cannula contained within the lumen of the sheath but not the sheath itself.

Figure 9A:
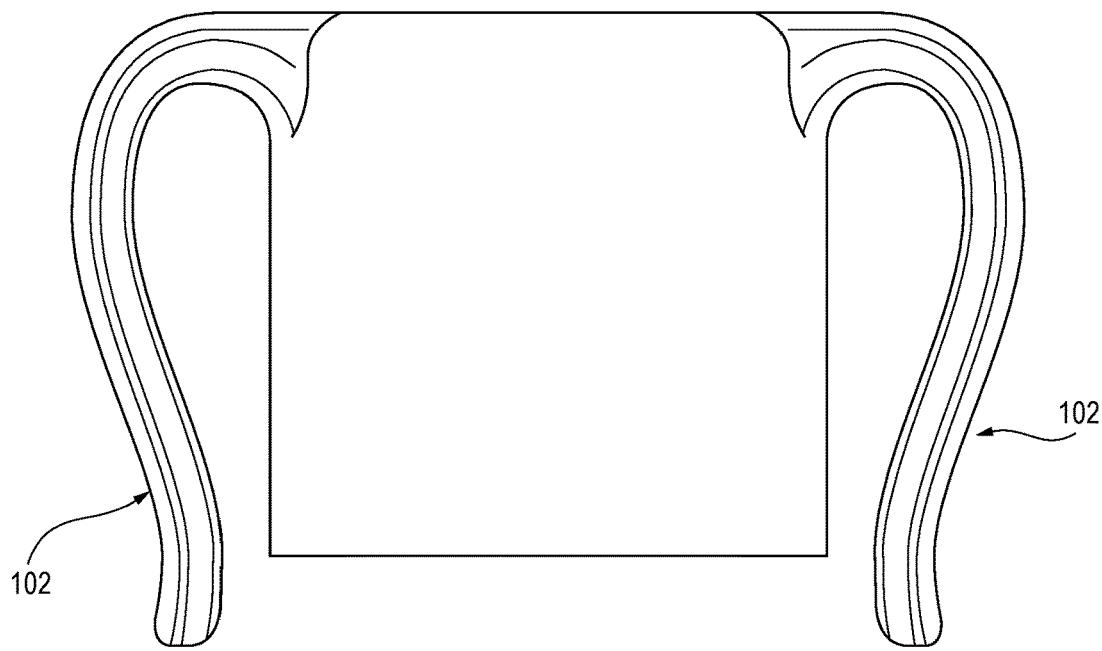
FIG. 9(A) is an illustration showing clips at an end of one embodiment of a sample retrieval device of the present invention.
Figure 9B:
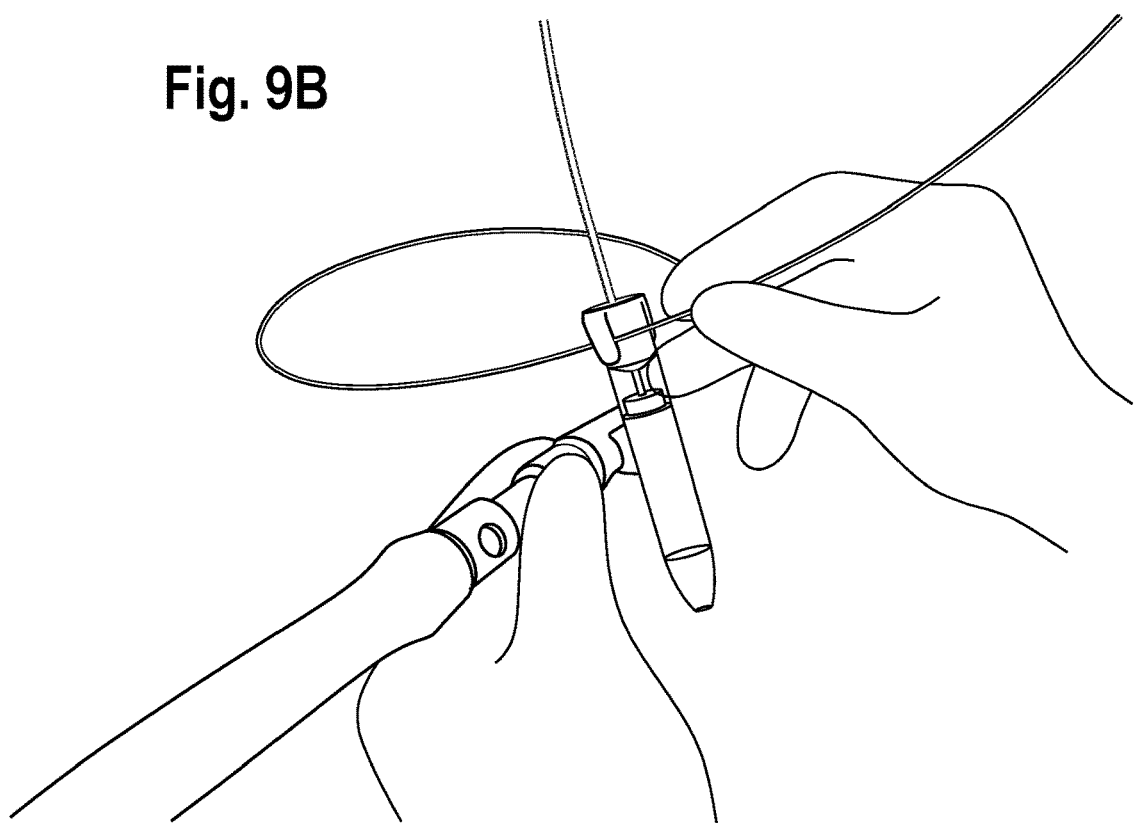
FIG. 9(B) illustrates a sheath of a biopsy needle looped through one of the clips of one embodiment of a sample retrieval device.

In one embodiment the top of the device, for example component 100, includes at least one sheath clip 102. Sheath clip(s) 102, also shown in FIG. 9(A), allow the user to loop the sheath through the clip(s) to hold the sheath in place and by doing so give more control over the procedure and reduces the risk of contamination. FIG. 9(B) illustrates the sheath looped through one of the clips.

Figure 3B:
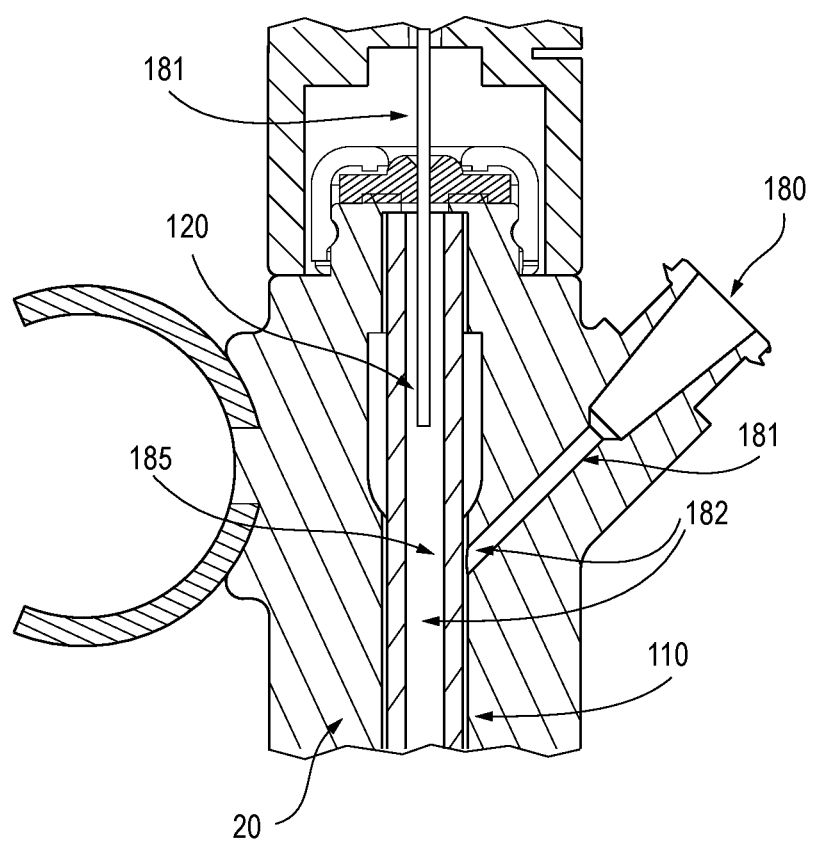
FIG. 3(B) is a cross section view of a sample retrieval device according to another embodiment of the present invention. The embodiment in FIG. 3(B) includes a flushing port.

FIG. 3(B) shows a partial cross-section view of another embodiment of a sample retrieval device. In this embodiment, sample retrieval device 20 includes a flushing port 180. Channel 181 provides for fluid access to lumen 110, enabling the delivery of flushing fluid into the lumen. In FIG. 3(B), biopsy needle sheath 120 is positioned within lumen 110 with its distal end below non-return valve 184. Needle cannula 185 is extended from sheath 120 and extends into the distal region of the device.

The user may attach a syringe or a similar device to port 180 and flush the distal (lower) region of the retrieval device with a fluid 182, for example, air, saline, cytolyt or hydrogen peroxide, to flush the outside of the needle cannula.

Figure 4:
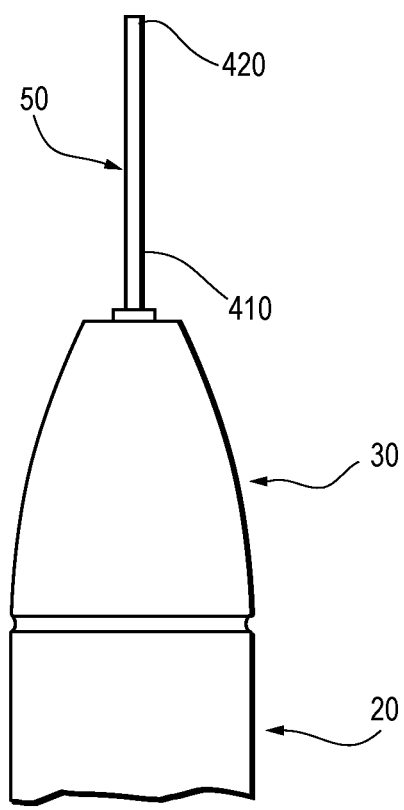
FIG. 4 is an illustration of the distal end of a sample retrieval device according to one embodiment of the present invention.

Turning now to FIG. 4, there is here illustrated an enlarged view of second end 30 of one embodiment of the device. Here, retrieval cannula 50 extends from second end 30 and is shown to be translucent or transparent, allowing the user to view the lumen of this cannula. For example, retrieval cannula may be formed from a hard transparent material like glass, such as borosilicate glass, or a polymer, such as polycarbonate. The use of a hard material will reduce the risk of the needle cannula getting caught on the inside wall of the lumen during extension or retraction of the cannula. In other embodiments, retrieval cannula 50 is opaque.

The use of a transparent retrieval cannula may provide for a magnifying effect, allowing for better visualization of the needle cannula. In some embodiments, a wide retrieval cannula also aids visualization of the needle cannula.

Biopsy needle cannula 410 is shown positioned within the lumen of retrieval cannula 50. Distal end 420 is positioned near the end of retrieval cannula 50. Preferably, the length of the retrieval cannula is sufficient to enclose the needle tip when the needle is fully extended and the sheath is positioned at the engaged position. However, the length should not be so long so as to make expelling of the sample difficult. In some embodiments, the distal end of the retrieval cannula is provided with a bevel (a needle-like bevel) to provide for easier expelling of the sample.

Typically, the cannula of a biopsy needle, such as biopsy needle cannula 410, is movable within the lumen of a sheath between a retracted position, where the distal end to the needle cannula is contained within the sheath, and an extended position, where the distal end of the needle cannula extends from the distal end of the sheath. In one embodiment of the sample retrieval device, retrieval cannula 50 extends from the device for such a length that when the distal end of the sheath is positioned at the engaged position and the needle cannula is at the fully extended position, the distal end of the needle cannula is contained within the retrieval cannula. Preferably, when the needle cannula is in the fully extended position, the distal end of the needle cannula is positioned near the end of the retrieval cannula.

Figure 11A:
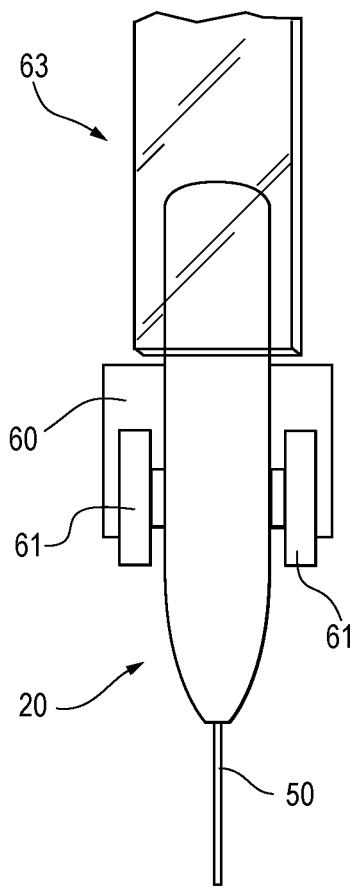
FIGS. 11(A) and 11(B) illustrate the positioning of the flash guard.
Figure 11B:
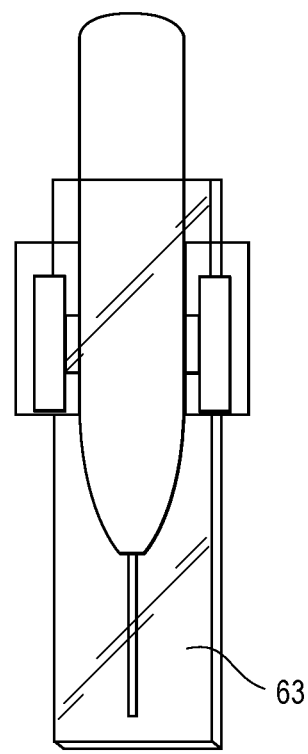
Figure 11C:
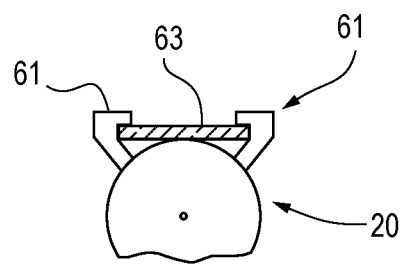
FIG. 11(C) is a transverse cross section of FIG. 11(B).

Turning now to FIG. 11(A-C), here is illustrated another embodiment of a sample retrieval device of the present invention. In this embodiment, sample retrieval device 10 includes a splash guard 63 that can be positioned to extend over the end of retrieval cannula 50. For example, the splash guard may be held in place by extension arms 61 extending from the body of the sample retrieval device. In one embodiment, the splash guard may be formed from glass or plastic and have the shape of a microscope slide. For example, as illustrated in FIGS. 11(A-C), splash guard 63 may be slid onto the sample retrieval device and held in position between the top surface of the device and the bottom surfaces of extension arms 61. In one embodiment, at least the portion of the splash guard extending over the end of retrieval cannula 50 is transparent, allowing the user to view the end of the cannula. In a preferred embodiment, the complete splash guard is transparent.

The presence of the splash guard protects against possible contamination during EUS FNA/FNB procedures, particularly when making slides for ROSE. If material is expelled too quickly or without warning from the needle, any material that splashes from the slide under preparation will be contained by the underside of the splash guard, hence reducing the risk of any contamination.

As will be disclosed in more detail below, the sheath of a biopsy needle is positioned at the engaged position within the sample retrieval device. In some embodiments, the distal end of the sheath is held in place by friction alone or by one of the mechanism disclosed above. In other embodiments, the sample retrieval device includes one of the mechanisms disclosed below to correctly position the distal end of the sheath at the engaged position and hold it securely in place. The mechanism ensures that the sheath does not exit from the sample retrieval device while the needle is exposed.

Figure 12A:
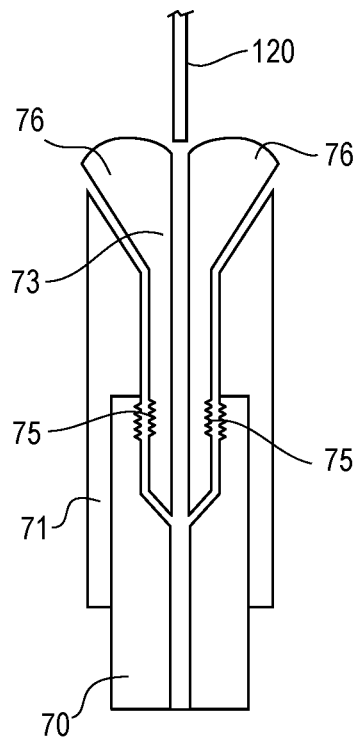
FIG. 12(A-B) are illustrations showing one embodiment of a mechanism for holding a sheath within the lumen of the sample retrieval device.
Figure 12B:
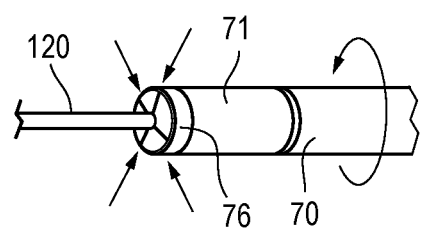

FIG. 12(A-B) shows one embodiment of a mechanism for holding the sheath in position. FIG. 12(A) shows a cross-section view of the mechanism. Here, the sample retrieval device includes a main body element 70 forming the lower portion of the retrieval device and a collar element 71 that rotates independently of element 70. Element 70 engages upper element 73 at screw mechanism 75. Flanges 76 of upper element 73 are positioned within the upper portion of element 71. When element 70 is rotated relative to element 73, element 73 it either moves downward against the upper portion of element 71 or moves upwards and away from the upper portion of element 71 (depending on the direction of rotation). Downward movement of element 73 results in flanges 73 to be pressed against the upper portion of element 71 and results in the flanges moving together and holding sheath 120 in the lumen of the device. FIG. 12(b) shows sheath 120 positioned in the device with flanges 76 preventing movement of the sheath.

Figure 13A:
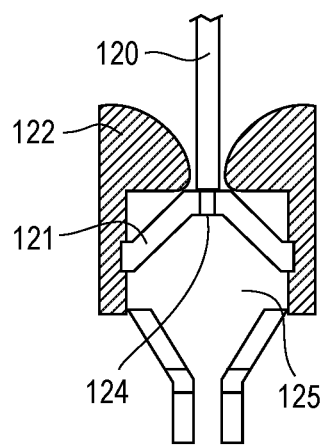
FIG. 13(A-B) are illustrations showing another embodiment of a mechanism for holding a sheath within the lumen of the sample retrieval device.
Figure 13B:
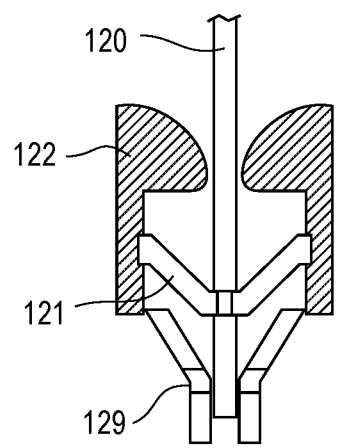

FIGS. 13(A-B) illustrate another mechanism for holding sheath 120 in place within the sample retrieval device. Here, the sample retrieval device includes diaphragm 121 held in position within chamber 125 defined by manifold 122. In one embodiment, chamber 125 is positioned above the non-return valve, in-line with the sample retrieval device lumen. Diaphragm 121 includes port 124, which is of a size to accommodate sheath 120 in a tight fit and allow the sheath to pass through it. The diaphragm has an extended position, as illustrated in FIG. 13(A), and a collapsed position, as illustrated in FIG. 13(B).

Normally, the diaphragm is in the extended position when sheath 120 is inserted into chamber 125 to position the distal end of the sheath at port 124. When enough force is applied to diaphragm 121 by the sheath, it will buckle into a collapsed position, as illustrated in FIG. 13(B), and lock around the sheath, holding it in position. The sheath may be released from the locking mechanism by applying enough force to unbuckle the diaphragm and return it to its extended position. The user will feel resistance from the diaphragm when sheath 120 is inserted into port 124 and will also feel a change in resistance when the diaphragm moves from the extended to the collapsed position. Thus, as well as providing a locking mechanism, this embodiment will also provide haptic feedback to the user, indicating that the sheath is inserted or released from the diaphragm. Of course, the device may also include viewing port 129, providing visual conformation that the sheath is positioned correctly.

FIGS. 14(A-B) illustrate yet another mechanism for holding sheath 120 in the correct position within the sample retrieval device. In one embodiment, chamber 134 is positioned above the non-return valve, in-line with the sample retrieval device lumen. The chamber includes two locking members 131 and 132 held in position as illustrated in FIG. 14(A). Each locking member includes an upper portion 137 and a lower portion 138, which are joined at hinge 136. Both the upper and lower portions of each locking member include a locking barb 139.

Sheath 120 is inserted into the sample retrieval device as described herein and into chamber 134 as illustrated in FIG. 14(A). The distal end of sheath 120 in inserted until it contacts the lower ends 140 of locking members 131 and 132. Further insertion of sheath 120 into chamber 134 causes the lower ends of the locking members to be pushed apart as is illustrated in FIG. 14(B). This, in turn, causes hinges 136 to open and brings locking barbs 139 into contact with sheath 120. The locking barbs grip sheath 120 and lock it into position within the sample retrieval device.

After completion of the procedure, sheath 120 may be removed from the sample retrieval device by pulling the sheath to release it from the locking barbs and causing the locking members to disengage and return to the position illustrated in FIG. 14(A). In one embodiment, hinges 136 is biased towards the position shown in FIG. 14(A) and hence return to this position when sheath 120 is removed from the sample retrieval device.

Figure 15A:
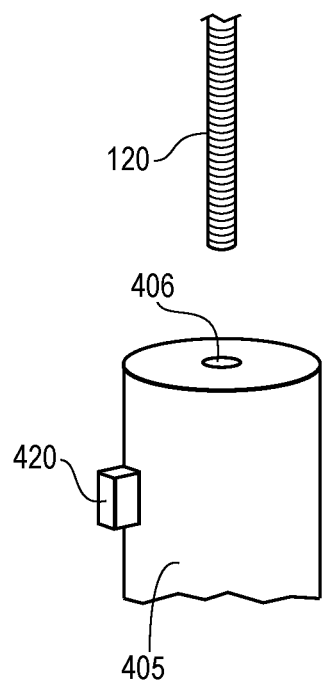
FIG. 15(A-C) are illustrations showing another embodiment of a mechanism for holding a sheath within the lumen of the sample retrieval device.
FIG. 15(B) and FIG. 15(C) are partial cross sections of FIG. 15(A).
Figure 15B:
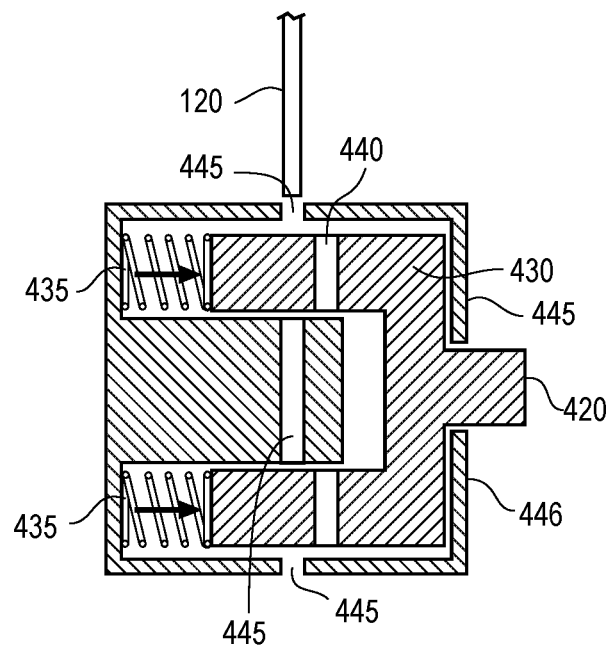
Figure 15C:
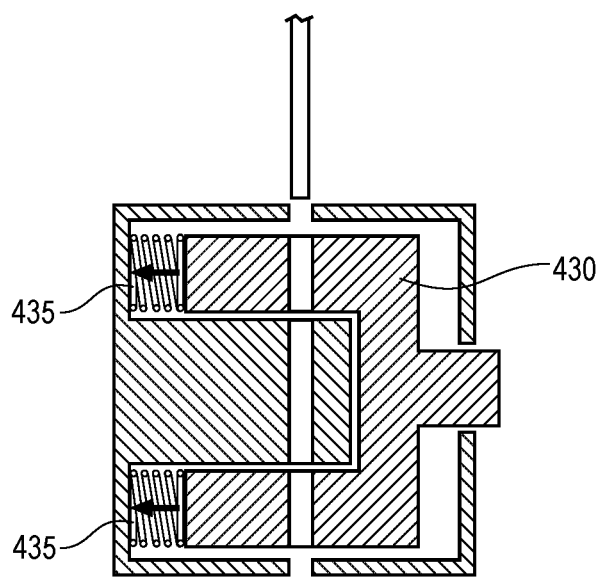

FIGS. 15(A-C) illustrate yet another mechanism for holding sheath 120 in the correct position within the sample retrieval device. FIG. 15(A) illustrates the distal end of sheath 120 positioned above the opening 406 of the lumen of sample retrieval device 405. In this embodiment, the device includes button 420, which connects to a closure member that is normally biased to a position extending into and closing the retrieval device lumen at a position above the non-return valve.

FIGS. 15(B-C) are cross-section views of the internal structure of the closure mechanism. Closure element 430 includes channel 440 which must be aligned with the lumen of the sample retrieval device to allow positioning of sheath 120 within the lumen. However, unless button 420 is pressed, springs 435 force member 430 against wall 446 of the device, resulting in channel 440 not being aligned with delivery channel 445. Such a configuration is illustrated in FIG. 15(B).

However, when button 420 is depressed, closure element 430 is moved away from wall 446 and channel 440 is aligned with lumen 445. Sheath 120 may then be positioned within the device at the correct position. Pressure on button 420 may then be released. Springs 435 will act to push closure element 430 towards wall 446 but are prevented from doing so by the presence of sheath 120 in the lumen of the device. After completion of the procedure, button 420 is again depressed to release the sheath and allow for removal of the sheath from the sample retrieval device.

FIGS. 16(A-C) illustrate a mechanism for straightening any bends in sheath 120 and for holding the sheath in the correct position within the sample retrieval device. Turning first to FIG. 16(A), there is illustrated one embodiment of sample retrieval device 610 including such a mechanism. In this embodiment, the portion of the device above the non-return valve is normally, but not necessarily, longer that in the embodiments previously disclosed.

FIG. 16(B) illustrates a partial cross section of the device, showing the internal construction of that portion of the device between the top entrance of retrieval device lumen 615 and non-return valve 616. This portion of the retrieval device lumen is lined with a series of rolling parts 620 (for example, ball bearings) which act to straighten the distal end of the sheath and enclosed needle cannula as it is inserted into and removed from the sample retrieval device lumen. FIG. 16(C) illustrates sheath 120 positioned with in the retrieval device lumen. Here, the sheath is held in place by rolling parts 620.

Figure 17A:
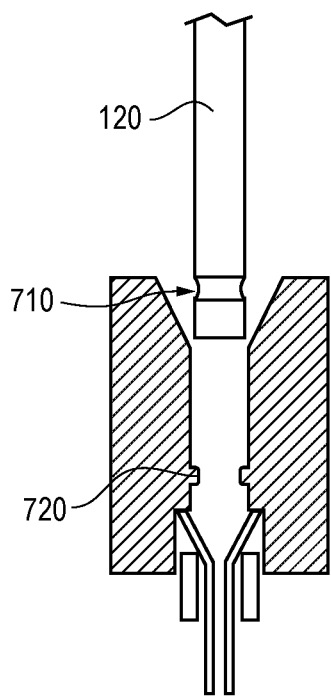
FIG. 17(A-B) are illustrations showing another embodiment of a mechanism for holding a sheath within the lumen of the sample retrieval device.
Figure 17B:
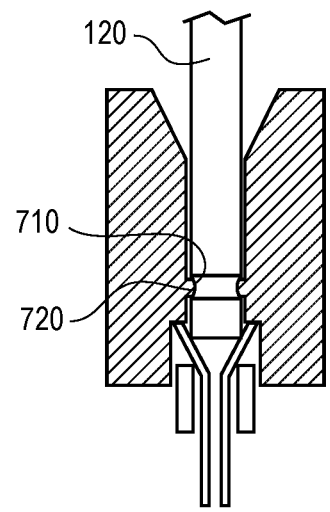

FIGS. 17(A-B) illustrate yet another mechanism for holding sheath 120 in the correct position within the sample retrieval device. Here, sheath 120 includes a ridge or cavity several millimeters back from the distal tip. The wall of the sample retrieval device lumen includes a corresponding ridge or cavity at a position such that these features line up when the tip of the sheath is positioned correctly within the lumen of the retrieval device. When the features are aligned, the user with detect a change in resistance as the ridge enters the cavity, confirming that the sheath is positioned correctly. FIG. 17(B) shows sheath positioned correctly within the lumen of the device.

In FIGS. 17(A-B) sheath 120 is shown to have a cavity 710 and the wall of the retrieval device lumen a corresponding ridge 720. Of course, the present invention also includes those embodiments where the sheath includes a ridge instead of a cavity and the lumen wall includes a corresponding cavity.

System for Needle Biopsy and Sample Retrieval

Another aspect of the present invention provides a system including a sample retrieval device as disclosed herein in combination with a biopsy needle. In one embodiment of such a system, the attachment member of the sample retrieval device is sized and shaped to engage a portion of the elongated body of the biopsy needle handle and to hold the sample retrieval device. For example, the attachment member may be sized and positioned to hold the longitudinal axis of the sample retrieval device perpendicular to the longitudinal axis of the biopsy needle.

The use of the sample retrieval device in combination with a biopsy needle addresses four problems associated with the retrieval of a sample from a biopsy needle. The device makes it possible for a single user to expel a sample from the needle. It also protects the needle during the procedure such that the needle is never exposed to air. This will reduce the risk of needle-stick injury to the user. The device will give the user significantly more control of the needle tip and sheath reducing the risk of cross contamination. Finally, the device protects the needle during the sample retrieval process reducing the risk of accidental kinking.

The system may include the sample retrieval device in combination with a variety of biopsy needle designs. For example, the retrieval device may be combined with a biopsy needle such as the needle disclosed in US Patent Publication Number 2014/0005478, published Jan. 2, 2014, the contents of which are incorporated by reference.

Figure 5:
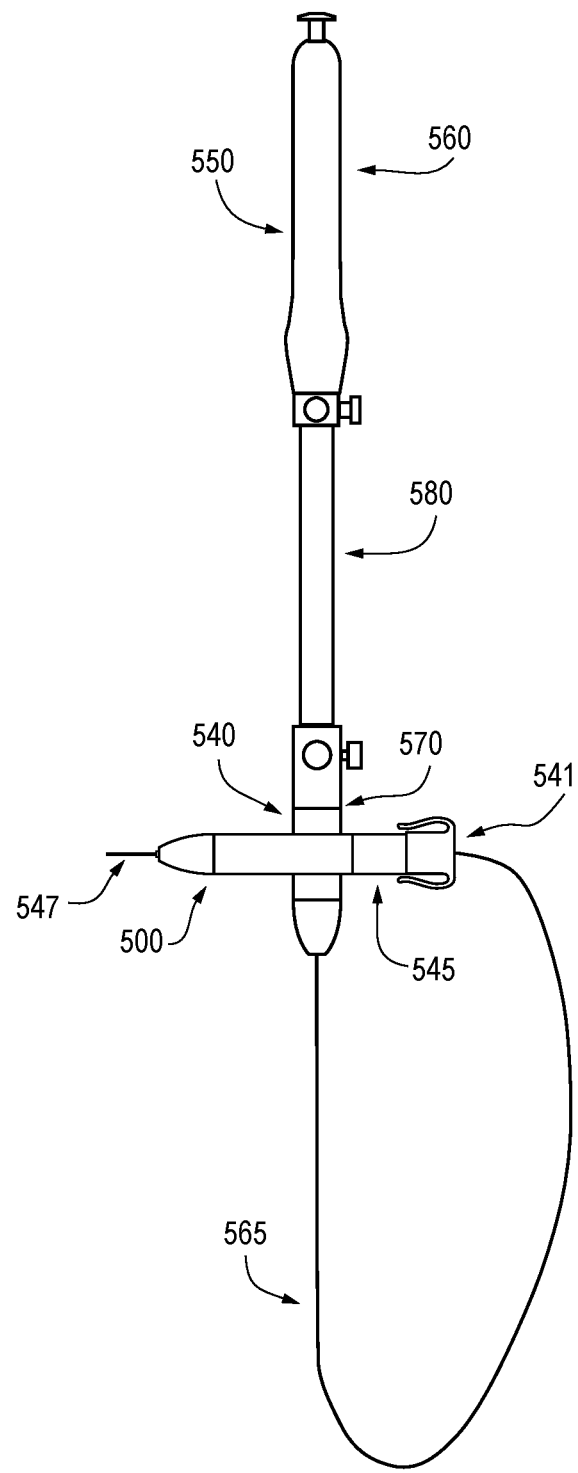
FIG. 5 is an illustration of a sample retrieval device according to one embodiment of the present invention. The sample retrieval device is shown while attached to a biopsy needle.

FIG. 5 illustrates one such system and includes sample retrieval device 500 and biopsy needle 550. Here, sample retrieval device 500 is illustrated as attached to biopsy needle 550 by attachment member 540. The biopsy needle includes a handle including proximal handle segment 560 and distal handle segment 570. FIG. 5 shows device 500 attached to distal handle segment 570. However in other embodiments, device 500 may attach to engagement portion 580.

Sheath 565 attaches to and extends distally from distal handle segment 570. An inner lumen (not shown) extends through the handle and sheath from the proximal end of proximal handle segment 560 to the distal end of sheath 565.

In FIG. 5, the distal end of sheath 565 is shown inserted into first end 541 of sample retrieval device 500. The distal tip of sheath 565 may be positioned within sample retrieval device 500 at a non-return valve (not-shown) positioned as described herein. Translucent or transparent member 545 is positioned so as to allow the user to view the non-return valve during the placement of the distal end of sheath 565 within the valve.

A biopsy needle cannula (not-shown) is positioned within the lumen of sheath 565. The needle cannula typically has open proximal and distal ends and a cannula lumen extending therebetween. In the embodiment illustrated in FIG. 5, proximal handle segment 560 may be slidably movable along engagement portion 580 of distal handle segment 570 between a proximal position, where proximal handle segment 560 is at a limit of its positioning away from distal handle segment 570 and a distal position, where proximal handle segment 560 is at a limit of its positioning towards distal handle segment 570.

A proximal portion of the needle cannula may be fixed to proximal handle segment 560 but free to move through the lumen of distal handle segment 570 and sheath 565 as proximal handle segment 560 is moved between its proximal and distal positions. In one embodiment, when proximal handle segment 560 is at the proximal limit of its movement along engagement portion 580, the distal end of the needle cannula is positioned within sheath 565. However, as proximal handle segment 560 is moved distally along engagement portion 580, the distal end of the needle cannula moves out of sheath 565.

If the distal end of sheath 565 is positioned at the engaged position within sample retrieval device 500, the needle cannula may extend from the non-return valve and along the portion of the retrieval device lumen between the non-return valve and retrieval cannula 547. In a preferred embodiment, the length of the needle cannula is such that, when the distal end of sheath 565 is positioned within the engaged position and proximal handle segment 560 is moved to its distal limit along engagement portion 580, the distal end of the needle cannula remains contained within retrieval cannula 547, preferably within the portion of retrieval cannula 547 extending from the body of the sample retrieval device.

Figure 18:
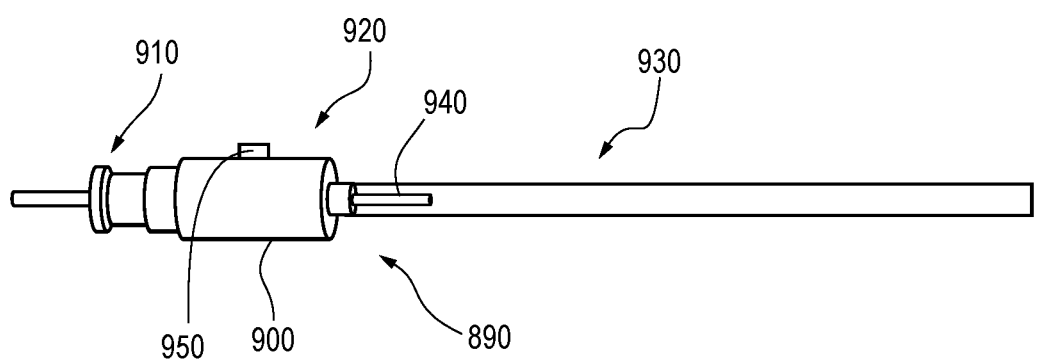
FIG. 18 is an illustration of a sample retrieval device according to another embodiment of the present invention.

FIG. 18 illustrates another embodiment of a sample retrieval device of the present invention. Sample retrieval device 890 includes an elongated body 900 having an endoscopy scope interface 920 at a distal end and a biopsy needle interface 910 at a proximal end. Retrieval cannula 930 extends from the distal end and serves the same purpose as the retrieval cannula disclosed above. Retrieval device 890 may also include an attachment member (not shown), such as the attachment members disclosed above.

Biopsy needle interface 910 releasably attaches to the distal end of a biopsy needle. For example, needle interface may attach to the sheath extender of the biopsy needle. In a preferred embodiment, the needle interface includes a luer connecter. For example, biopsy needle interface 910 may include a male luer connector at the proximal end which is sized to attach to a female luer connector on the biopsy needle. Endoscopy scope interface 920 releasably attaches to a proximal end of an endoscopy scope, preferably via a luer connection. For example, interface 920 may feature a female luer connector which will be attached to the scope during use. Retrieval cannula 930 preferably has an outside diameter that is compatible with the endoscopy scope and extends into the scope during use of the device.

FIG. 18 shows sheath 940 of a biopsy needle extending through the lumen of retrieval device 890 and into retrieval cannula 930. In one embodiment, sample retrieval device 890 is permanently attached to the sheath of the biopsy needle. In this embodiment, the user is prevented from using the biopsy needle cannot without having the safety mechanism in place.

Figures 19A, 19B:
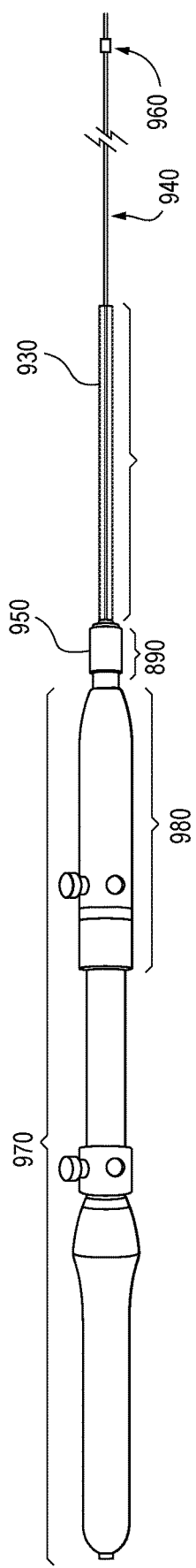
FIG. 19(B) is and enlarged view of the distal end of the sheath of the biopsy needle of FIG. 19(A).

FIG. 19(A) illustrates sample retrieval device 890 connected to extender sheath 980 the distal end of biopsy needle 970. Sheath 940 extends through the body of sample retrieval device 890 and through retrieval cannula 930. Stop 960 (shown in enlarged detail in FIG. 19(B)) is positioned near the distal end of sheath 940. When not attached to the biopsy needle, sample retrieval device 890 is free to slide along sheath 940 but is prevented from moving distally beyond stop 960.

Figure 20:
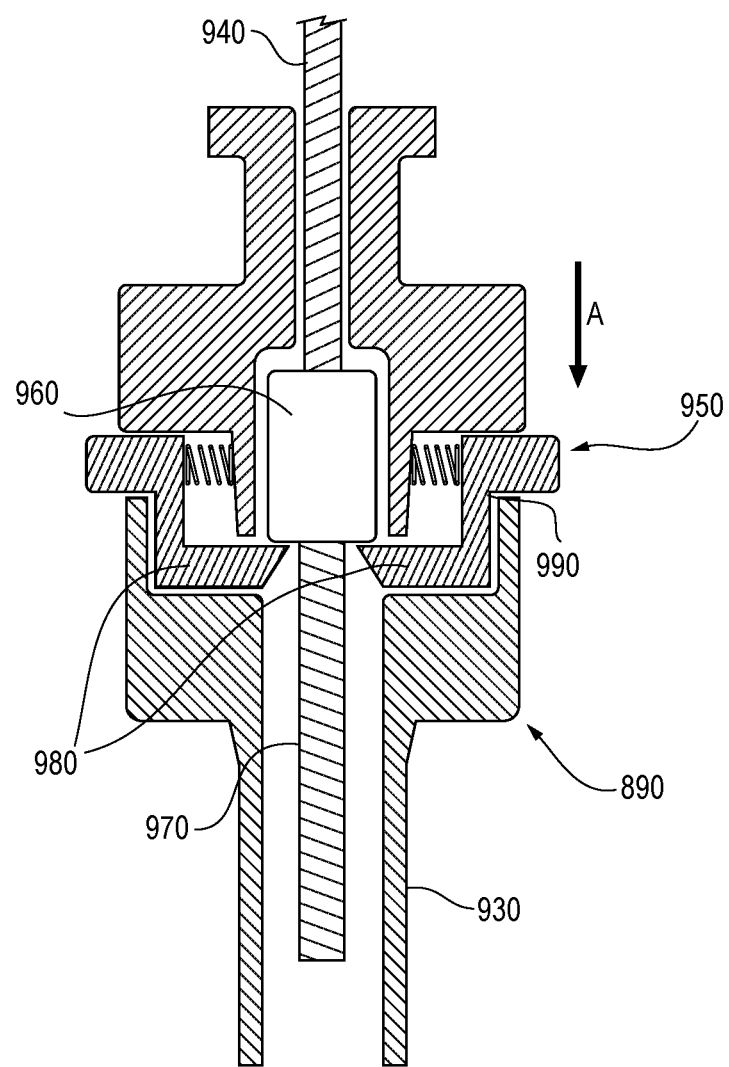
FIG. 20 is a cross-sectional view of one embodiment of a sample retrieval device of the present invention.

FIG. 20 shows a cross section view of one embodiment of sample retrieval device 890. Here, sheath 940 is positioned within lumen 970 of the device. Stop 960 is positioned within the expanded distal portion of lumen 970. Locking mechanism 990 enables stop 960 to be locked in position within sample retrieval device 890. In FIG. 20, locking mechanism is shown in the locked position. Release button 950 may be activated to withdraw leavers 980 from lumen 970 and allow stop 960 to move distally (in the direction of allow "A") so that the distal end of sheath 940 may be extended distally beyond sample retrieval device 890. Levers 980 may be tapered as shown in FIG. 20 so to allow stop 960 to snap back into position within retrieval device 890 when the retrieval device is again positioned at the distal tip of sheath 940.

When stop 960 is locked into position within retrieval device 890, retrieval cannula 930 is preferably of sufficient length to enclose the distal end of the needle cannula of the biopsy needle when the needle cannula is at it fully extended position. In certain embodiments, the locking mechanism may provide an audial or tactile indication to the used that the stop is locked into position within the lumen of the sample retrieval device. Other known locking mechanisms may be used in place of the mechanism described above. All that in required is that the sample retrieval device is restrained from moving beyond the distal end of the sheath and that the stop may be releasably positioned in the lumen of the retrieval device.

Although the system including the sample retrieval device has been described with reference to the needle cannula movement mechanism illustrated in FIG. 5, the present embodiments encompass those including an alternative design of biopsy needle. The sample retrieval device may be used with any biopsy needle so long as the outer dimension of the biopsy needle sheath is such that the sheath can be inserted into the lumen of sample retrieval device and held at the non-return valve and that the dimension of the needle cannula is such that it may be extended through the retrieval cannula.

Further examples of biopsy needles that may be combined with the sample retrieval device include the EchoTip Ultra® and EchoTip ProCore® needles (Cook Ireland Ltd., Limerick, Ireland). Typically, the external size of the needle cannula is in the range of 19-gauge to 25-gauge. The outer dimension of the sheath will be slightly large so as to accommodate such a needle cannula.

Method of Sample Retrieval from a Biopsy Needle

Figure 6:
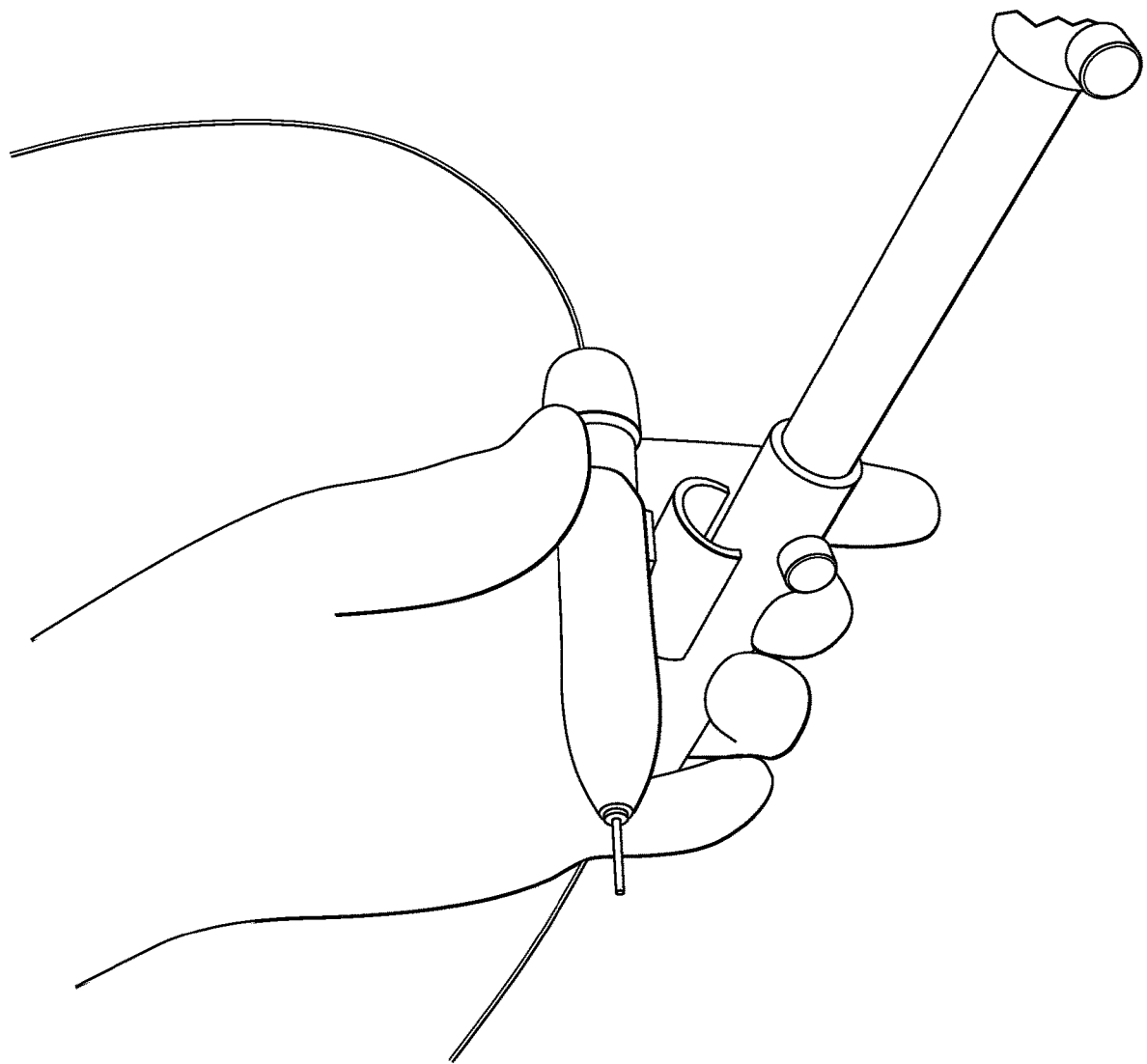
FIG. 6 illustrates the attachment of one embodiment of a sample retrieval device to a biopsy needle.

Another aspect of the present invention provides a method of retrieving a sample from a biopsy needle utilizing a sample retrieval device as disclosed herein. The following method is applicable for use with the sample retrieval device shown in FIG. 1. The biopsy needle containing the sample, for example a cytology sample, is attached to the sample retrieval device by attaching the handle of the biopsy needle to the retrieval device as illustrated in FIG. 6. The sheath of the biopsy needle may be inserted into the retrieval device before or after the needle is attached to the retrieval device. Likewise, if a stylet is positioned within the needle cannula, this may be removed before or after the biopsy needle is attached to the sample retrieval device. A stylet may be positioned in the lumen during the process of positioning the needle within the patient to stiffen the needle cannula and to prevent debris from accumulating within the needle cannula.

With the sheath in position, the biopsy needle cannula is extended to position the distal tip of the needle cannula within the retrieval cannula of the sample retrieval device. A slide or other surface is then provided and the sample positioned on the surface for evaluation. For example, in the Rose technique the sample is applied to a cytology slide.

Typically, the sample is expelled from the needle cannula by the application of air pressure to the proximal end of the needle cannula. For example, a syringe may be attached to the lumen at the proximal end of the handle of the biopsy needle and pressure applied by inserting the syringe plunger into the barrel of the syringe.

In certain cases, multiple flushing of the needle cannula, with air and/or fluid (for example saline), may be required to fully expel the sample from the biopsy needle cannula. After the sample is fully expelled, the stylet may be reinserted into the needle cannula and the needle cannula retracted into the sheath. The distal end of the sheath may be removed from the sample retrieval device and the device unattached from the handle of the biopsy needle.

Figure 7:
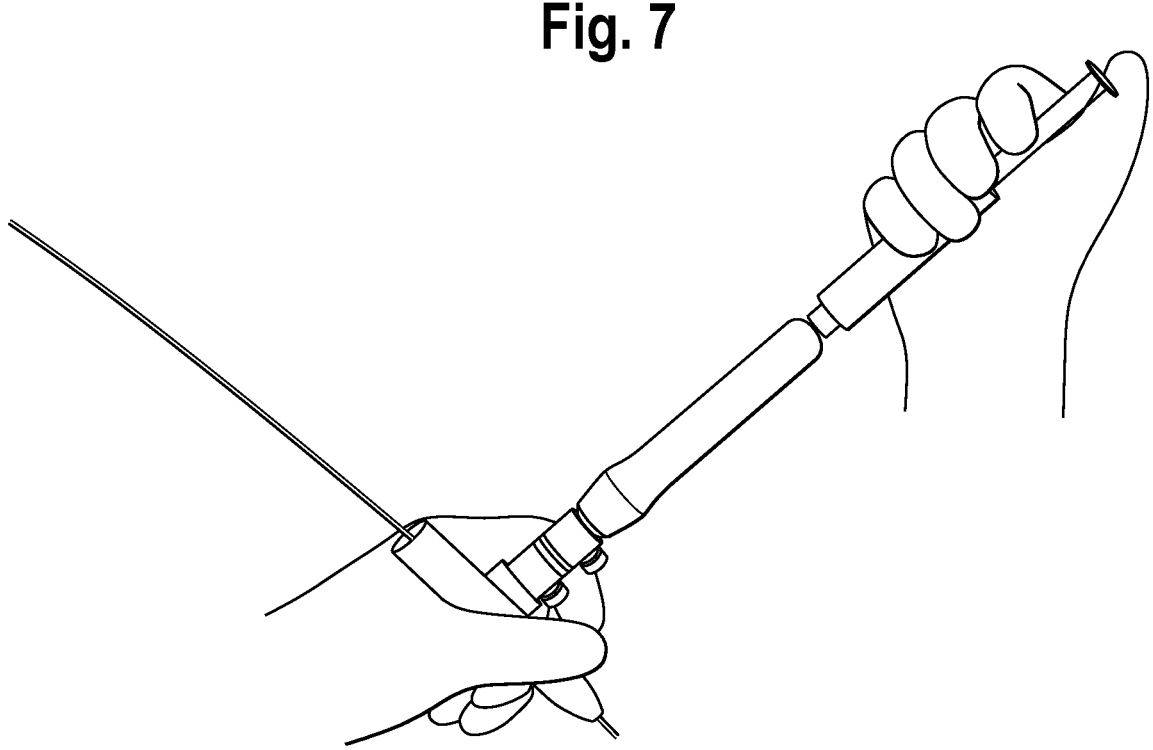
FIG. 7 illustrates the use of one embodiment of a sample retrieval device in combination with a biopsy needle.
Figure 8:
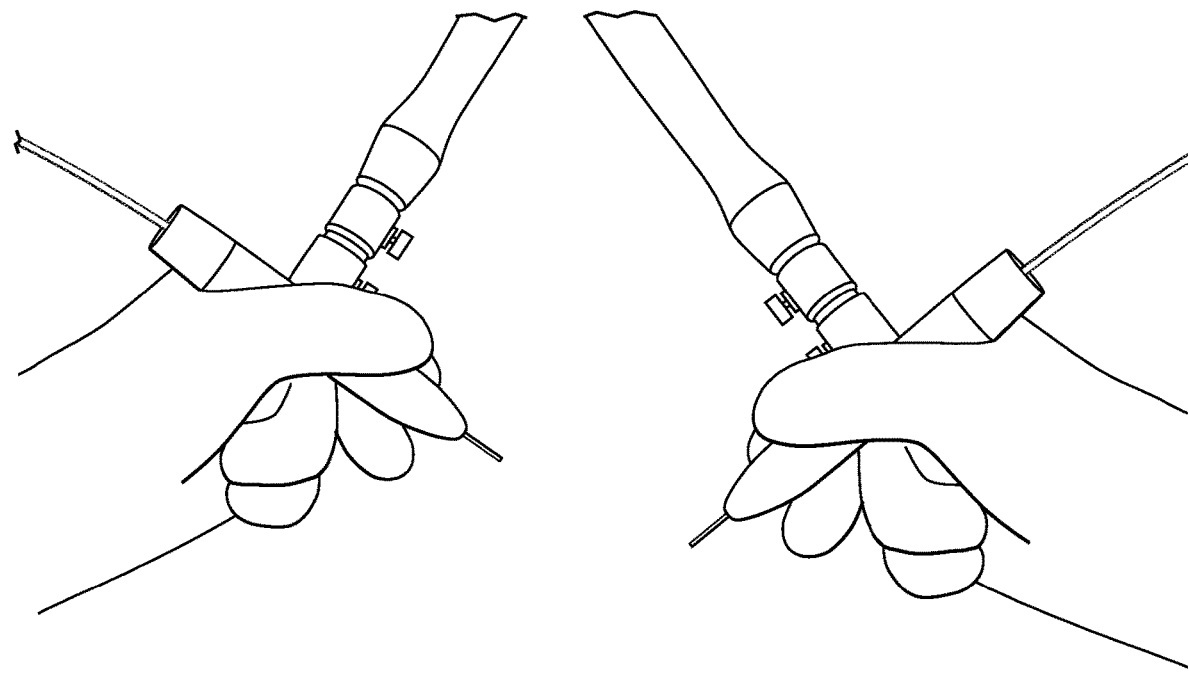
FIG. 8 illustrates the use of one embodiment of a sample retrieval device in combination with a biopsy needle. The photographs illustrate the use of the combination by a right-handed and a left-handed user.

The sample retrieval device removes several steps from the current procedure and allows the procedure to be performed by a single user. The device gives the user simultaneous control over both the needle handle and the needle tip while making the sheath of the needle more manageable. As can be seen from FIG. 7, control of the needle's handle, tip and syringe attachments can be attained by a single user, unlike the situation in current procedures, which require at least two users. The use of the sample retrieval device grants a single user full control of the sample retrieval process. The device also greatly reduces the risk of both needle-stick injury and contamination. FIG. 8 illustrates that the device also offers the additional advantage of being capable of use by both right-handed and left-handed users.

The following method is applicable for use with the sample retrieval system shown in FIG. 19(A). The distal end of the biopsy needle (extender) is attached to the proximal end of the retrieval device and the distal end of the retrieval device attached to the endoscope, resulting in the sheath being inserted into the endoscope. The endoscopy procedure is then performed as normal.

Upon completion of the procedure, the distal end of the biopsy needle is detached from the sample retrieval device, leaving the retrieval device attached to the endoscope. The biopsy needle is then withdrawn until the stop of the sheath is positioned within the lumen of the sample retrieval device. Preferably the user is alerted of the correct positioning of the stop of an audible ("Click") or tactile indication.

The sample retrieval device may then be removed from the endoscope. With the stop locked in position within the sample retrieval device, the cannula of the biopsy needle is protected by the retrieval cannula. The user may then deliver the sample from the biopsy needle as described above with reference to the sample retrieval device of FIG. 1. If the sample retrieval device 890 is provided with an attachment device, it may be attached to the handle of the biopsy needle as illustrated, for example, in FIG. 6.

Kit Including a Sample Retrieval Device and a Biopsy Needle

Another aspect of the present invention provides a kit including the sample retrieval device as disclosed above and a biopsy needle, which may be packaged separately or together in a single container. These components may be supplied in a sterilized condition. In one embodiment, the biopsy needle is a EchoTip ProCore® HD Ultrasound Biopsy Needle (Cook Ireland Ltd., Limerick, Ireland) The kit may also contain a syringe for use in sample retrieval. In one embodiment, the components of the kit are contained in recesses of a tray base having a peel-back lid.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. A system comprising:
   a biopsy needle comprising:
   a handle comprising a proximal handle segment and a distal handle segment;
   a sheath attaching to and extending distally from the distal handle segment, wherein a lumen extends through the handle and sheath from a proximal end of the proximal handle segment to a distal end of the sheath; and
   a biopsy needle cannula positioned within the lumen and having open proximal and distal ends and a cannula lumen extending therebetween, wherein the biopsy needle cannula is slidably movable through a portion of the lumen between a first position wherein a distal end of the biopsy needle cannula is positioned within the lumen of the sheath and a second position wherein the distal end of the biopsy needle cannula extends distally from the sheath,
   and
   a sample retrieval device comprising:
   an elongated body having a longitudinal axis extending from a first end to a second end;
   a retrieval cannula positioned within the elongated body and extending from the second end;
   a retrieval device lumen extending from the first end to the second end and through the retrieval cannula, wherein a portion of the retrieval device lumen at the first end is sized to accept the sheath and to hold a distal end of the sheath and wherein a portion of the retrieval device lumen at the second end and through the retrieval cannula is sized to accept the biopsy needle cannula;
   a non-return valve positioned within the elongated body and in line with the retrieval device lumen, and
   an attachment member attaching to the elongated body, wherein the attachment member is sized to attach to and hold the handle.

2. The system of claim 1, wherein the attachment member is sized to attach to and hold the handle at a substantially perpendicular orientation to the longitudinal axis of the sample retrieval device.

3. The system of claim 1, wherein the proximal handle segment slidably engages the distal handle segment, wherein the proximal end of the biopsy needle cannula attaches to the proximal handle segment and wherein the retrieval cannula is of a length sufficient to enclose the distal end of the biopsy needle cannula when the proximal handle segment slidably engages the distal handle segment at a fully distal position and when the distal end of the sheath is positioned at an engaged position within retrieval device lumen.

4. The system of claim 1, further comprising a stylet sized to be slidably movable within the biopsy needle cannula lumen.

\* \* \* \* \*